United States Patent [19]

Foster

[11] Patent Number: 5,194,388
[45] Date of Patent: Mar. 16, 1993

[54] "KAPPA" NUMBER CALIBRATION STANDARD

[75] Inventor: James J. Foster, Clifton Forge, Va.

[73] Assignee: Westvaco Corporation, New York, N.Y.

[21] Appl. No.: 377,278

[22] Filed: Jul. 10, 1989

[51] Int. Cl.$^5$ .......................... G01N 31/00; D21C 3/20
[52] U.S. Cl. ........................................... 436/8; 162/72
[58] Field of Search ..................... 436/8–16; 162/72

[56] References Cited

U.S. PATENT DOCUMENTS

| | | |
|---|---|---|
| 3,674,434 | 7/1972 | Pottenger . |
| 4,345,913 | 8/1982 | Jönsson . |
| 4,540,468 | 9/1985 | Genco et al. . |
| 4,743,339 | 5/1988 | Faix et al. . |
| 4,746,401 | 5/1988 | Roberts et al. ............ 162/72 |
| 4,752,357 | 6/1988 | Baker . |
| 4,780,182 | 10/1988 | Baker . |

OTHER PUBLICATIONS

Fisher '86 catalog pp. 1168, 1166.
Michael A. Paulonis, "Kappa number and overall yield calculation based on digester liquor analysis," Nov., 1988 Tappi Journal, p. 184.

Primary Examiner—James C. Housel
Assistant Examiner—N. Bhat
Attorney, Agent, or Firm—W. A. Marcontell; R. L. Schmalz

[57] ABSTRACT

Instruments for determining the degree of delignification corresponding to a sample of kraft or soda process digested wood pulp are calibrated with a predetermined quantity of refined lignin. For convenient use and application, a standardized solution comprising such refined lignin and an organic solvent such as ethylene glycol may be prepared for distribution to use points. Such standardized refined lignin, whether tested as a powdered solid or as a standardized solution yields a consistent "K" Number, "Permanganate" Number, "Kappa" Number or "Klason" Number value from standardized titration test procedures.

2 Claims, 3 Drawing Sheets

Lignin vs K No.

Encapsulated Lignin vs K No.

No Temperature Cycling

One Temperature Cycle Between 0° & 100° C

Two Temperature Cycles
Between 0° & 100° C

"KAPPA" NUMBER CALIBRATION STANDARD

BACKGROUND OF THE INVENTION

1. Field of Invention

The present invention relates to the art of pulp and papermaking from natural, cellulosic materials, More particularly, the invention addresses the science of evaluating the precise degree of delignification to which a cellulosic material has been subjected.

2. Background of the Invention

Natural cellulose for pulp and papermaking is obtained from wood and other herbaceous sources by numerous processes of delignification. Lignin is a constituent of the pitch or gum substance which binds cellulose fiber together to form an integral, composite organism. By means of thermochemical digestion, the gum material is hydrolyzed and separated from the cellulose by water washing and screening.

Two such thermochemical digestion processes widely practiced at present are the kraft and soda processes. By the kraft process, wood is cooked, under heat and pressure, in the presence of a blended solution of sodium hydroxide and sodium sulfide. The soda process is similar but the chemically active compound is exclusively sodium hydroxide.

By either process, the active chemicals react with both the gum and the cellulose, but at different rates. Strong, easily bleached paper fiber is therefore the product of compromise between maximum gum hydrolysis opposed to minimum cellulose destruction.

In the course of commercial pulp production, a working ratio of wood quantity to cooking solution is derived by a combination of analysis and experience. The number of variable parameters relevant to an exact chemical constituency, temperature and time required for a specific digester charge of wood chips to achieve a predetermined degree of gum hydrolysis defies precision. Time or length of cook therefore becomes the final control variable for a specific digester charge.

The consistency to which cellulose is separated from the natural gum directly affects both the strength and whiteness of a paper product laid from the resulting pulp. If cooked too long, the pulp and, hence, paper is weak. If insufficiently cooked, excessive bleaching chemical is required to achieve a predetermined degree of whiteness.

To this end, several standardized tests have been developed to quantify the degree to which gum associated with cellulose has been hydrolyzed. Such tests are predicated on the relative quantity of non-hydrolyzed lignin that remains in natural association with a sample quantity of water-washed pulp. The "Kappa" Number test, defined by TAPPI Standard T-236 OS-76 determines the volumetric quantity of 0.1 Normal potassium permanganate solution consumed by 1 gram of washed pulp in 10 minutes at 25° C. The "Kappa" Number is 50% of the permanganate volume, in milliters, consumed. The percent of lignin remaining in association with the pulp is $$\text{lignin \%} = 0.147 \times \text{"Kappa" Number}$$

Another such residual lignin test is the "K" Number or "Permanganate" Number test which is a specialized permutation or abbreviation of the "Kappa" Number test.

Traditionally, "Kappa" Number and "K" Number tests are performed manually in a chemical laboratory. More recently, automated instruments have been developed to perform the tests automatically: either from pulp "grab" samples from the process flow stream at the washers, for example, or from pulp samples taken "on-line" from a digester blow line. In either case, these automatic "Kappa" Number or "K" Number instruments are computer controlled, electro-mechanical devices that are required to operate in hostile environments. Consequently, such "Kappa" Number or "K" Number instruments are subject to calibration drift.

The prior practice of "Kappa" Number or "K" Number instrument calibration required that a single pulp sample batch be "Kappa" Number or "K" Number tested in both the instrument and the laboratory. The laboratory result was taken as the control test, and the instrument result was adjusted to correspond to it. This calibration procedure was both slow and expensive.

An objective of the present invention, therefore, is to provide a stable sample solution that will yield a consistent "Kappa" Number or "K" Number value regardless of the test procedure used.

Another object of the present invention is to provide a stable calibration solution for automatic "Kappa" Number or "K" Number instruments.

INVENTION SUMMARY

These and other objects of the invention, as will subsequently become apparent, are accomplished by a predetermined quantity of refined lignin placed in the reaction 1 vessel portion of the selected automatic titration test instrument. To expedite measurement of the precise quantity of lignin placed in the instrument reaction vessel, a solution of refined lignin such as INDULIN TM AT (RC) dissolved in an organic solvent such as ethylene glycol may be used. Following an aging interval of about 5 weeks, such a solution will yield a substantially constant "Kappa" Number or "K" Number value responsive to the standard TAPPI T-236 OS-76 test procedure.

As an alternative test preparation procedure, a measured quantity of lignin compatible with the instrument test sample volume and desired index number may be isolated by containment within a gelatin capsule. When an instrument calibration test is desired, contents of a capsule are emptied into the instrument reaction vessel.

DETAILED DESCRIPTION

In application, a user of the present invention requires knowledge of the exact weight of refined lignin necessary to produce a predetermined "Kappa" Number or "K" Number value in his particular instrument. The calibration "Kappa" Number or "K" Number may be arbitrarily selected but usually is that of the instrument mid-scale value, or of the production target number.

It should be noted that, definitively, the "Kappa" Number and "K" Number tests use a 1 gm b.d.w. (bone dry weight) test sample quantity of washed pulp. The test and "Kappa" or "K" Number value addresses the weight quantity of lignin retained by said 1 gm pulp sample.

Figure 1:
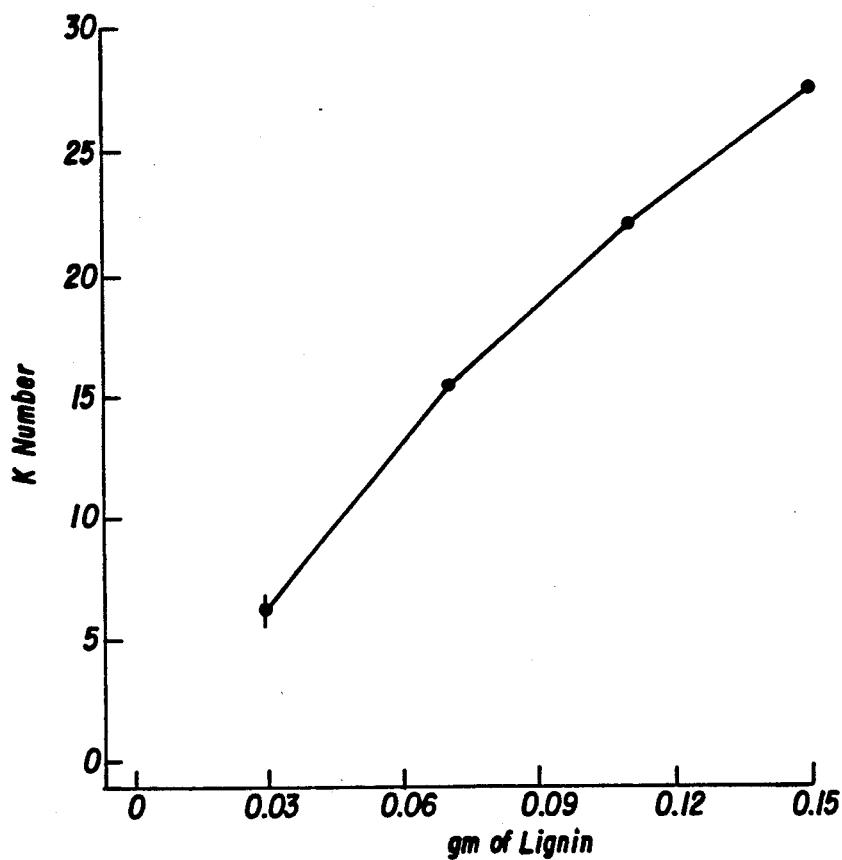
FIGS. 1 and 2 are graphs of the relationship between "K" Number values and corresponding weights of refined, powdered lignin.

To this end, a first set of experiments was conducted to determine the interaction between lignin and "K" Number analysis. The terms "K" Number and "Permanganate" Number are synonymous and frequently used interchangeably by the art. Although "Kappa" Number designates a slightly different test, the fundamental parametric relationships reported herein are the same. For the first test series, four different sample weights of INDULIN TM AT(RC), a refined lignin product of Westvaco Corporation, Charleston, S.C., ranging from 30 to 150 mg were tested in random order. Triplicate tests were run on each sample weight. FIG. 1 illustrates the results of these tests which resulted in an overall pooled standard deviation of 0.43 "K" Number units.

This FIG. 1 graph indicates a nearly linear relationship between refined lignin content and "K" Number: a relationship that is qualitatively similar to that found by V. Berzins and J. E. Tasman, "The Permangnate Consumption of Pulp Materials," Pulp and Paper Magazine of Canada, 58(10), 145(1957). Berzins and Tasman compared the "Kappa" Number, of pulp samples to a lignin content determined by the Klason Method. Although the relationship is qualitatively similar, it is not identical. The primary difference is that the powdered, refined lignin of the present experiments provided a "K" Number index that was 70% lower than the index derived from pulp sample lignin determined by the Klason method. The difference is reconciled by mass transfer limitations inside the powdered lignin particles. While developing the FIG. 1 data, lignin powder residual was found at the bottom of the reaction vessel following each "K" Number analysis. The unreacted lignin powder residual may account for the 70% lower "K" Number result.

Figure 2:
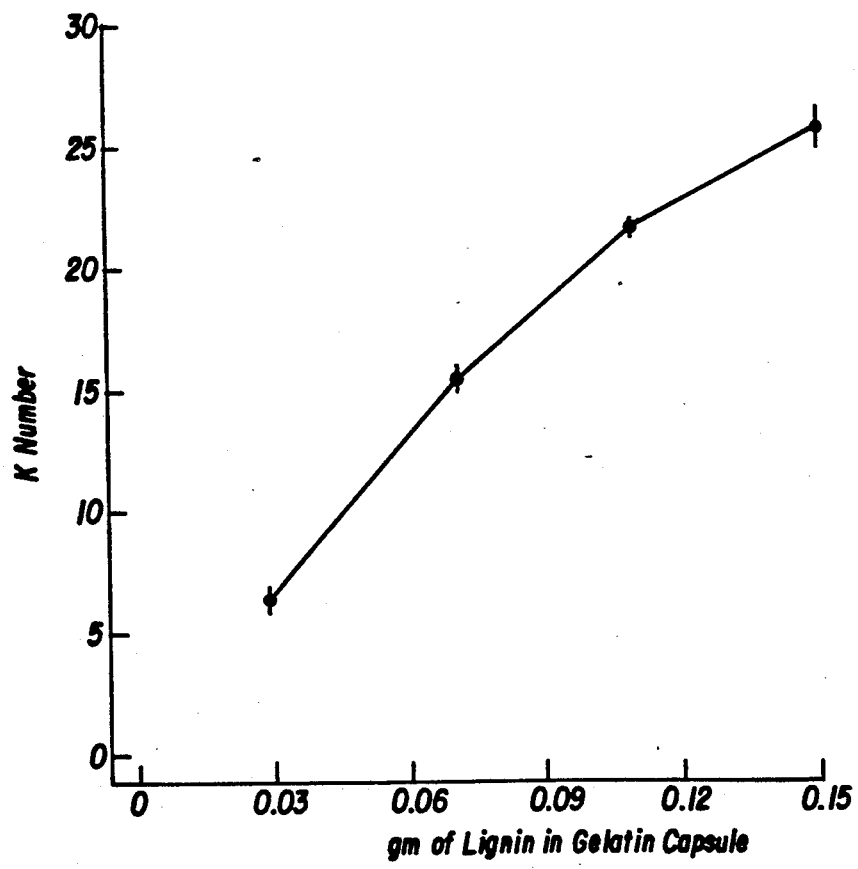

Due to the physical difficulty of measuring and handling 30 to 150 milligram quantities of lignin powder in an industrial plant environment, a second experimental set was designed whereby the previous experiment triplicate quantities of four target weight samples were encapsulated in separate gelatin capsules. FIG. 2 illustrates the results of this second experiment set. The FIG. 2 graph has the same qualitative features of FIG. 1 but resulted in greater data point scatter. The pooled standard deviation for this second experiment set was 0.863 "K" Number units: twice greater than the first experimental set.

A repetition of the second experimental set which included one minute of high speed blending prior to "K" Number analysis reduced the pooled standard deviation to 0.44 "K" Number units.

In further pursuit of an efficient delivery system for refined lignin as an instrument calibration standard in an industrial plant environment, a third set of experiments was designed about liquid solvents of lignin that were compatible with the "K" Number analysis. Lignin solvents include dioxane, ethylene glycol, monoethanolamine, dimethyl formamide and Cellosolve.

The "Kappa" Number and "K" Number analyses are performed with acidic permanganate. Consequently high pH solvents cannot be used due to interference with the analysis. Dioxane was found to react in a non-reproducible manner with the "K" Number analysis. Ethylene Glycol reacts with acidic permanganate, but it reacts consistently and only to a minor degree. Moreover, ethylene glycol is relatively safe to handle. Consequently, ethylene glycol was preliminarily found to conform with the specified need. Stability of a lignin-/ethylene glycol solution as to time, temperature and cycling was determined by a Box-Behnken response surface statistical experiment with 4 replicates per experiment and a total of 60 experimental runs.

The Experimental solution consisted of 3.698 gm of INDULIN TM AT(RC) research grade pine kraft lignin powder per liter of reagent grade ethylene glycol. 5 ml of this solution was used for each "K" Number analysis. The concentration was formulated to give a "K" Number of 12.5 per 5 ml of solution using the 1 gm of wood pulp sample relation:

$$gm\ lignin = 0.00147\ (\text{``K'' Number})$$

From this experiment, it was shown that the three variables of time, temperature and thermal shock (cycles between temperature extremes) had a weak effect on the "K" Number result. Of the three variables, time had the greatest effect. The raw experimental data produced an average "K" Number value of 12.00 within a total range of 2.33 "K" Number units and a pooled standard deviation of 0.253.

Figure 3:
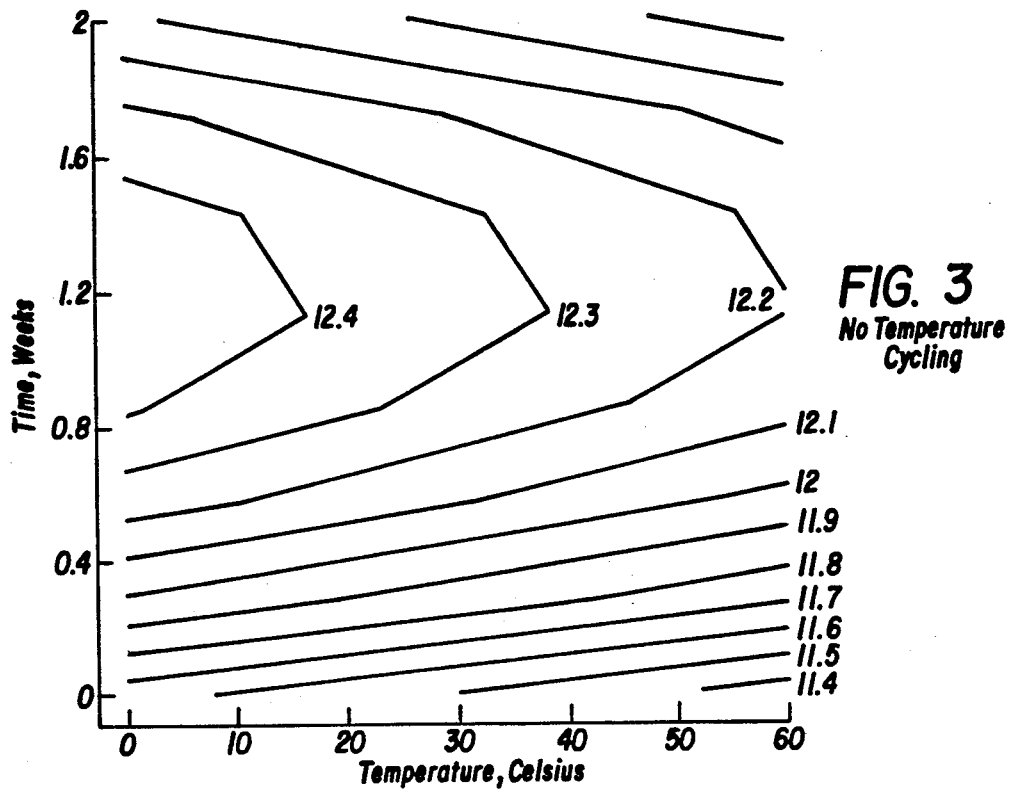
FIGS. 3, 4 and 5 are contour graphs illustrating the "K" Number value dynamics relative to time and temperature; and, FIG. 6 is a graph of the relationship between "K" Number values and time over a 16 week evaluation interval.

FIG. 3 is a contour plot of the data with no temperature cycling. At room temperature, freshly made lignin-/ethylene glycol solution had a "K" Number of 11.5. Eight days later, the "K" Number peaked at 12.3. At the end of 2 weeks, the "K" Number value had fallen to 11.9.

Figure 4:
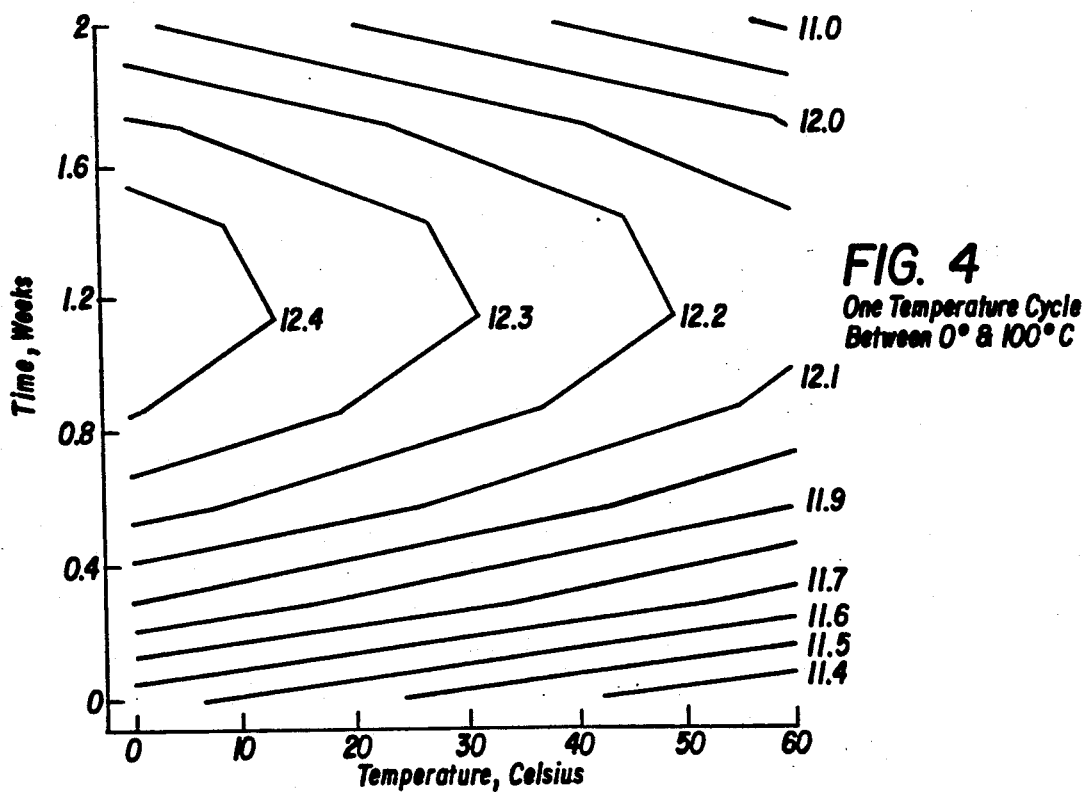
Figure 5:
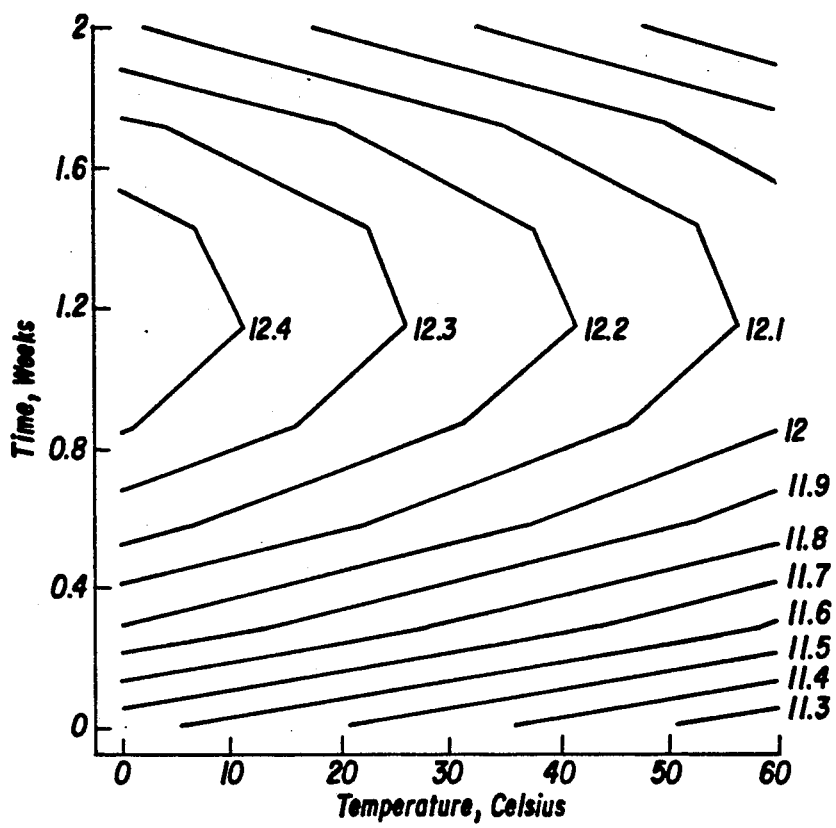

The features of FIGS. 4 and 5 are essentially the same as those of FIG. 3. A comparison of FIGS. 3 and 4, however, will reveal a marginal effect of temperature cycling.

Figure 6:
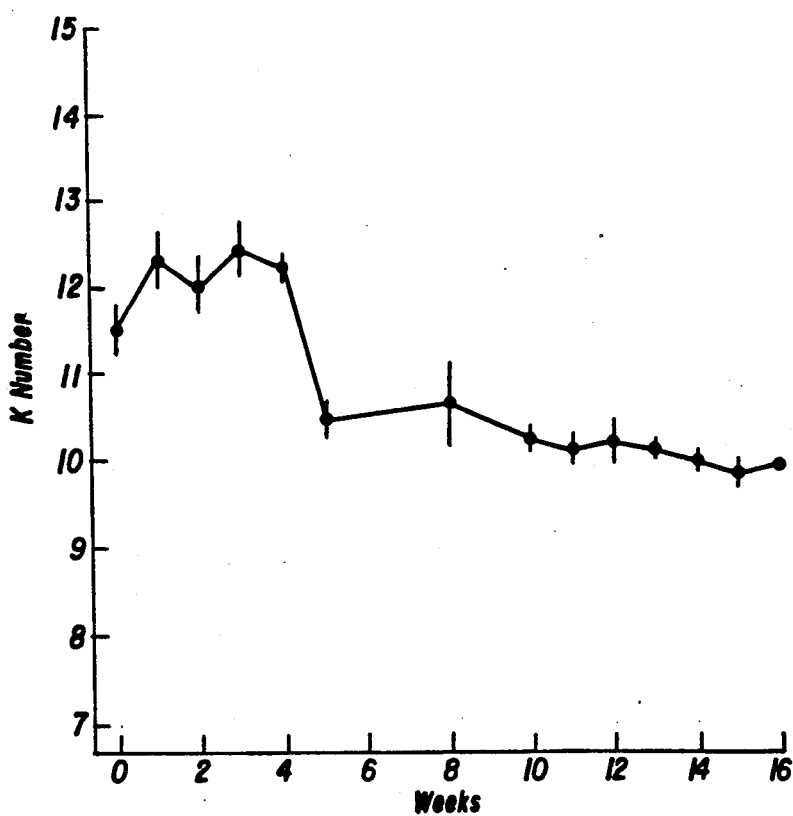

It being determined by the aforedescribed third experimental set that a lignin/ethylene glycol solution system was unstable in time, a fourth experimental set was designed to investigate long term aging. Using the same 3.698 gm of INDULIN TM AT(RC) lignin powder per liter of ethylene glycol, a 16 week statistical experiment was performed. FIG. 6 illustrates the result.

FIG. 6 represents 95% statistical confidence level data taken for 16 weeks at 30° C. with no temperature cycling. Over the first 4 weeks, the solution "K" Number increased from 11.50 to 12.23. After the fifth week, however, the "K" Number value had leveled off and remained essentially constant.

This FIG. 6 data suggests the occurrence of a reaction within the lignin/ethylene glycol solution during the first five weeks after formulation. After the fifth week, the reaction is substantially complete and the "K" Number value stabilizes. Although a very slow "K" Number value degradation continues after the fifth week, such decline amounted to only 0.6 "K" Number unit by the sixteenth week: small in comparison to "K" Number variations from pulp samples.

Having fully described my invention, obvious variations will readily occur to those of ordinary skill in the art. Therefore,

I claim:

1. A method of calibrating instruments designed to directly measure the relative quantity of residual lignin intimately associated with a digested cellulosic pulp comprising the steps of:

a) determining the quantity of digested and washed cellulose pulp appropriate for an instrument test sequence;

b) determining the quantity of refined lignin corresponding to said quantity of pulp having a predetermined residual lignin index value;

c) charging a residual lignin measuring instrument sample vessel with said quantity of refined lignin;

d) cycling an instrument test sequence of said solution; and e) adjusting said instrument to report a test value corresponding to said predetermined residual lignin index value;

said quantity of refined lignin is dissolved in solution with a lignin solvent; said solution of lignin and said solvent is aged by about five weeks.

2. A method of calibrating instruments for directly measuring residual lignin intimately associated with a digested paper pulp comprising the steps of:

a) preparing a substantially stabilized solution of refined lignin and organic lignin solvent;

b) charging a residual lignin measuring instrument sample vessel with an appropriate quantity of said solution having a known residual lignin index value;

c) cycling an instrument test of said solution; and d) adjusting said instrument to report a test value corresponding to said known solution value;

said solution is stabilized before using by an aging interval of about five weeks.

* * * * *